United States Patent [19]

Hartley et al.

[11] 4,101,579
[45] Jul. 18, 1978

[54] PHENETHANOLAMINE ETHERS

[75] Inventors: David Hartley; Lawrence Henry Charles Lunts; David Trevor Collin, all of London, England

[73] Assignee: Allen & Hanburys Limited, London, United Kingdom

[21] Appl. No.: 706,619

[22] Filed: Jul. 19, 1976

Related U.S. Application Data

[63] Continuation of Ser. No. 527,306, Nov. 26, 1974, abandoned, which is a continuation of Ser. No. 307,623, Nov. 17, 1972, abandoned, which is a continuation of Ser. No. 6,591, Jan. 28, 1970, abandoned.

[30] Foreign Application Priority Data

Feb. 6, 1969 [GB] United Kingdom ............ 6379/69

[51] Int. Cl.² .......................................... C07C 103/29
[52] U.S. Cl. ........................... 260/559 R; 260/559 A
[58] Field of Search ....................... 260/559 R, 559 A

[56] References Cited

U.S. PATENT DOCUMENTS

| 3,483,221 | 12/1969 | Wilhelm et al. ............ 260/326.14 T |
| 3,644,353 | 2/1972 | Lunts et al. .................... 260/559 |
| 3,644,520 | 2/1972 | Hartley et al. ................. 260/559 |

OTHER PUBLICATIONS

Crowther et al., J. Med. Chem. vol. 11, pp. 1009–1013 (1968).
Howe et al., J. Med. Chem. vol. 11, pp. 1000–1012 (1968).
Grana et al., Il Farmaco Ed. Sc. vol. XXI, pp. 4–15 (1966).

*Primary Examiner*—C. Davis
*Attorney, Agent, or Firm*—Bacon & Thomas

[57] ABSTRACT

Compounds of the general formula I and physiologically acceptable acid addition salts thereof:-

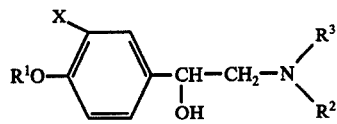

in which $R^1$ is a lower alkyl, lower alkenyl, or arylalkyl radical, which radicals may optionally be substituted by one or more alkoxy or hydroxy groups.
$R^2$ represents a hydrogen atom or a lower alkyl radical which may optionally be substituted by one or more hydroxy groups, amino groups, or heterocyclic rings containing one or more heteroatoms, or $R^2$ represents a cycloalkyl, arylalkyl or aryloxyalkyl radical, which radicals may optionally be substituted by one or more alkoxy or hydroxy groups;
$R^3$ represents a hydrogen atom or a benzyl group;
X represents a group of formula —$CONR^4R^5$ where $R^4$ and $R^5$ may be the same or different and each represents hydrogen or a lower alkyl group;
with the proviso that when $R^2$ is tertiary butyl and $R^1$ is a benzyl group, $R^3$ represents a hydrogen atom. The compounds have a blocking action on β-adrenergic receptors and in some cases an antagonising effect on α-adrenergic receptors.

4 Claims, No Drawings

PHENETHANOLAMINE ETHERS

This application is a continuation of application Ser. No. 527,306, filed Nov. 26, 1974, and now abandoned, which is in turn a continuation of application Ser. No. 307,623, filed Nov. 17, 1972 and now abandoned, which is in turn a continuation of application Ser. No. 6,591, filed Jan. 28, 1970 and now abandoned.

This invention relates to novel phenylethanolamine derivatives possessing useful biological activity and to compositions containing the same.

The present invention provides compounds of the general formula 1 and physiologically acceptable acid addition salts thereof:

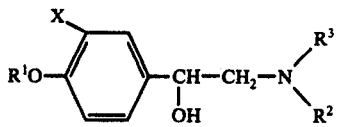    I in which $R^1$ is a lower alkyl, lower alkenyl, or arylalkyl radical, which radicals may optionally be substituted by one or more alkoxy or hydroxy groups;

$R^2$ represents a hydrogen atom or a lower alkyl radical which may optionally be substituted by one or more hydroxy groups, amino groups, or heterocyclic rings containing one or more heteroatoms, or $R^2$ represents a cycloalkyl, arylalkyl or aryloxyalkyl radical, which radicals may optionally be substituted by one or more alkoxy or hydroxy groups;

$R^3$ represents a hydrogen atom or a benzyl group;

X represents a group of formula $—CONR^4R^5$ where $R^4$ and $R^5$ may be the same or different and each represents hydrogen or a lower alkyl group;

with the proviso that when $R^2$ is tertiary butyl and $R^1$ is a benzyl group, $R^3$ represents a hydrogen atom.

The lower alkyl and alkenyl radicals referred to above all contain from 1 to 6 carbon atoms, preferably 1 to 4 carbon atoms and they may have a straight or branched carbon chain.

As the compounds of general formula I possess at least one asymmetric carbon atom, the invention also includes all the possible optically active forms and racemic mixtures of the compounds. Racemic compounds may be resolved by conventional methods, for example by salt formation with an optically active acid, followed by fractional crystallisation.

Diastereoisomeric mixtures may be separated by fractional crystallisation of the bases of their acid salts.

The compounds of the invention have been found to possess a potent blocking action on β-adrenergic receptors, and in addition some of the compounds are also capable of antagonising α-adrenergic receptors. The compounds which are β-adrenergic blocking agents are of use in the treatment and prophylaxis of cardiovascular disorders, e.g. angina pectoris, and may also be useful in protecting the heart against tachycardia induced by drugs or exercise. The compounds which possess both α- and β- blocking properties may be used as hypotensive agent and also in the treatment of peripheral disorders such as Raynaud's disease, with minimal side effects. They are also of value in the treatment of angina pectoris.

Thus, for example, in the anaesthetised dog, 5-[1-hydroxy-2-(1-methyl-3-phenylpropyl)aminoethyl]-o-anisamide at 1 mg/kg i.v. completely abolished the tachycardia produced by intravenous isoprenaline and reduced the response to injected moradrenaline by 62%. In in vitro tests on the antagonism of the isoprenaline-induced increase in force of contraction of electrically-driven Guinea-pig atria the compound had a $pA_2$ value of 8.1 compared with 7.9 for the β-blocker propranolol. The compound had a $pA_2$ value of 6.0 in antagonising moradrenaline-induced contractions of the rat vas deferens. Phentolamine which is a standard α-blocker has $pA_2$ 6.9 in this preparation. In the conscious renal hypertensive dog the compound produced a fall in blood pressure of a5 - 30 mm Hg after oral doses of 1 - 2 mg/kg.

In contrast, although the corresponding allyl ether (1; $R_1 = CH_2 = CHCH_2—R_2 = CHMe.CH_2.CH\ 2Ph$, $R_3 = H$, $X = CONH_2$) given i.v. at 1 mg/kg to the anaesthetised dog completely blocked the β-adrenergic responses to isoprenaline the α-responses to injected noradrenaline were reduced by only about 20%.

Specific preferred compounds are those the preparation of which is described in the Examples.

The compounds may be formulated for use in human or veterinary medicine for therapeutic or prophylactic purposes. The invention therefore includes within its scope pharmaceutical compositions comprising as active ingredient compounds of general formula 1 or physiologically acceptable addition salts thereof. Preferred salts include the hydrochloride, sulphate, maleate, acetate, fumarate, lactate and citrate. Such compositions may be presented for use in a conventional manner with the aid of carriers or excipients and formulatory agents as required, and with or without supplementary medicinal agents. These compositions include, for instance, solid or liquid preparations for oral use, suppositories and injections. Oral administration is most convenient in the form of tablets which may be prepared according to conventional methods and may be coated if desired. Injections may be formulated with the aid of physiologically acceptable carriers and agents as solutions, suspensions, or as dry products for reconstitution before use. The doses of the active ingredient which may be used may vary within a wide range. Suitable doses are generally within the range of 5 mg to 1000 mg, preferably 20 mg to 200 mg.

The compounds of the present invention may be prepared by a number of processes.

In one process, the compounds of the invention are prepared by reacting the ketones of the general formula II with an amine $NHR^2R^3$ in a solvent, for example, benzene or ethyl methyl ketone to form the aminoketones of formula III, which yield the compounds of the invention on reduction of the ketone group by conventional methods, with for example hydrogen and a noble metal catalyst, or a complex metal hydride such as sodium borohydride.

In a modification of this process, the carbonyl group of the haloketone may be reduced to a —CHOH group before condensation with the amine $NHR^2R^3$

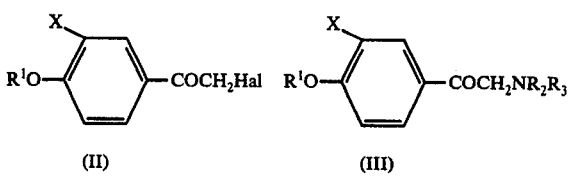

(II)   (III)

The compounds of the invention in which $R^2$ and/or $R^3$ are hydrogen may be obtained from compounds of formula I or III in which $R^2$ and/or $R^3$ are benzyl by reduction with hydrogen and a noble metal catalyst.

The compounds of the invention may also be prepared by reacting a halide of formula $R^1Hal$ with a phenol derivative of general formula IV and then reducing the carbonyl group. In a modification of this process the phenol IV, is first converted into an alkali metal salt to facilitate the reaction with the halide $R^1Hal$.

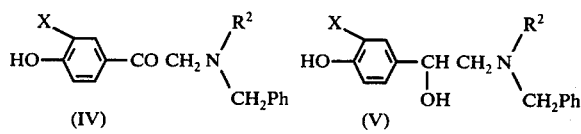

Alternatively, the phenol IV may be reduced to the alcohol V, for example with sodium borohydride, before condensation with the halide $R^1Hal$.

The compounds of the invention in which $R^2$ is not hydrogen may also be prepared by alkylation of the compounds in which $R^2$ and $R^3$ are hydrogen atoms by condensation with a carbonyl compound followed by reduction of the azomethine so formed, with, for example, a complex metal hydride, such as sodium borohydride, or hydrogen and a noble metal catalyst.

It will of course, be understood that the above processes can be carried out where X is a group, for example, alkoxy carbonyl, that can be converted into the group X as previously defined by treatment with an amine $NHR_4R_5$. This conversion can be affected at any convenient stage, for example, on intermediates such as (1) or (111) where X is alkoxy carbonyl.

The following examples illustrate the invention.

EXAMPLE 1

5-(2-tert-Butylamino-1-hydroxyethyl)-o-anisamide, hydrochloride (a) A solution of 5-bromoacetyl-o- anisic acid, methyl ester (5.74 g) and N-benzyl tert. butylamine (6.4g) in methyl ethyl ketone (100 ml) was refluxed for 5 hours. The N-benzyl-tert.butylamine hydrobromide was filtered off and the filtrate evaporated to dryness. The residue was triturated with ether and a further small amount of the amine hydrobromide separated (4.65g). The ether solution was treated with an ethereal solution of hydrogen chloride and the gummy precipitate crystallised from ethyl acetate, containing a few drops of methanol, to afford 5-(N-benzyl-N-tert.butylglycyl)-o-anisic acid, methyl ester, hydrochloride (8.0g) m.p. 178.179°. Recrystallisation from ethyl acetate-methanol gave 4.4 g, m.p. 181°-3° (with dec.)

(b) 5-(N-Benzyl-N-tert.butylglycyl)-o-anisic acid, methyl ester, hydrochloride (4.05g) in ethanol (60 ml) was added to a pre-reduced suspension of 10% Pd/C (1.0g) in ethanol (15 ml) and hydrogenated until uptake ceased (hydrogen uptake was 441.cc). The catalyst was filtered off and the filtrate evaporated to dryness to afford 5-(2-tert.butylamino-1-hydroxyethyl)-o-anisic acid, methyl ester, hydrochloride as a white crystalline solid (2.9g) m.p. 189°-194°.

(c) 5-(2-tert.butylamino-1-hydroxyethyl)-o-anisic acid, methyl ester, hydrochloride (2.39g) was dissolved in water, basified with sodium bicarbonate solution and extracted with chloroform. The chloroform extracts were washed with brine, dried over sodium sulphate, and evaporated to dryness to afford the free base as a colourless gum (2.1g) which crystallised on standing, m.p. 195°-197° (from benzene).

This amine was dissolved in ethanol (10 ml) and ammonia (d 0.88) (20 ml), and allowed to stand at room temperature. After two days no starting material was present. The solution was then evaporated to dryness and digested with benzene to afford a colourless solid (1.45 g) m.p. 151°-155°. This base (1.3g) was dissolved in chloroform-ethanol (9:1) and treated with ethereal hydrogen chloride to afford 5-(2-tert.butylamino-1-hydroxyethyl)-o-anisamide, hydrochloride (1.2g) m.p. 241°-242°.

EXAMPLE 2

2-Benzyloxy-5-[1-hydroxy-2-(isopropylamino)ethyl benzamide]

(a) A solution of 2-benzyloxy-5-bromoacetylbenzoic acid, methyl ester (2 g) in methanol (50 ml) and tetrahydrofuran (100 ml) was cooled to 0°-10° and treated with sodium borohydride (0.75 g) with stirring. The resulting solution was stirred at room temperature for 1.5 hours, then evaporated to small volume, keeping the temperature at or below 15°. The solution was then treated with 2N hydrochloric acid (15 ml) and ice, giving a white suspension which was extracted with ether and dried. After evaporating the ether, the residue was dissolved in ethanol (25 ml); isopropylamine (2.5 ml) was added and this solution was refluxed overnight. Then the solvent and excess isopropylamine were evaporated and the residue was treated with dilute sodium hydroxide and extracted with ether. Drying and evaporation of the ether solution gave an oily residue which was dissolved in sodium-dried ether and treated with ethereal hydrogen chloride. This gave an oily precipitate which solidified on adding a little acetone and scratching with a glass rod. The solid (0.75g) had a non-sharp melting point, ~150°. Crystallisation from acetone gave white microcrystals of 2-benzyloxy-5-[1-hydroxy-2-(isopropylamino) ethyl] benzoic acid, methyl ester, hydrochloride (0.3g) m.p. 169°-170°.

(b) 2-Benzyloxy-5-[1-hydroxy-2-(isopropylamino)ethyl]benzoic acid, methyl ester, hydrochloride was basified giving a white crystalline solid, m.p. 112°-5°, and 0.5g of this was dissolved in methanol (10 ml) and treated with ammonia (d. 0.88) 5 ml). The resulting solution was left to stand at room temperature for 1 week. The solution was evaporated to dryness and the residue was triturated with ether, giving 2-benzyloxy-5-[1-hydroxy-2-(isopropylamino) ethyl] benzamide, as a white solid (0.42g), m.p. 135°-8°. Crystallisation from ethyl acetate raised the melting point to 142°-4°.

EXAMPLE 3

5-[1-hydroxy-2-(1-methyl-3-phenylpropyl)aminoethyl]-o-anisamide (a) A solution of 5-(N,N-dibenzylglycyl)-o-anisamide (3.88g) in tetrahydrofuran (25 ml) and ethanol (125ml) was added to a pre-reduced suspension of 10% Pd/C (1.0g) in ethanol (25 ml). Uptake of hydrogen ceased within 14 hours. The catalyst was filtered off and the solvent evaporated under reduced pressure to leave 5-(2-amino-1-hydroxyethyl)-o-anisamide as a colourless gum.

(b) To a solution of the above 5-(2-amino-1-hydroxyethyl)-o-anisamide in ethanol (70ml) was added benzyl acetone (1.5g), and the mixture was gently refluxed for 1 hour. The cooled solution was then added to a suspension of pre-reduced 5% platinum on charcoal (0.4g) in ethanol (10 ml) and hydrogenated until uptake was complete. Hydrogen uptake was complete within 14 hours. The catalyst and solvent were removed to leave 5-[1-hydroxy-2-(1-methyl-3-phenylpropyl)aminoethyl]-o-anisamide as an oil (2.36g) which slowly crystallised on rubbing with ether, m.p. 110°–148°.

The above material was recrystallised from tetrahydrofuran and benzene to give the product as a white solid, m.p. 110°–132°.

This diastereoisomeric mixture (5.3g) was crystallised 3 times from 74 o.p. ethanol to give a pure diastereoisomer (1.9g) m.p. 152°–154°. This yielded a hydrochloride m.p. 180°.

The liquors from the first crystallisation of the base were evaporated and the residue recrystallised from ethanol to give the other diastereoisomer of the base (900 mg) m.p. 120°–122°. Treatment with ethanolic hydrogen chloride gave the hydrochloride, m.p. 190°–192°.

EXAMPLE 4

2-(Benzyloxy)-5-(2-tertbutylamino-1-hydroxyethyl)-benzamide 5-(2-tert.butylamino-1-hydroxyethyl)-salicylamide hydrochloride (2.0g) in ethyl methyl ketone (50 ml) and anhydrous potassium carbonate (1.5 g) were refluxed together with stirring for ½ hour. Benzyl chloride (1.75 g) in ethyl methyl ketone (5 ml) was added dropwise with stirring and the mixture was refluxed for 17 hours. The potassium salts were filtered off and the filtrate was evaporated to dryness in vacuo leaving a cream solid which was crystallised from ethyl acetate to afford 2-(benzyloxy)-5-(2-tert. butylamino-1-hydroxyethyl)-benzamide as colourless needles (1.4g) m.p. 120° C.

EXAMPLE 5

5-(2-Amino-1-hydroxyethyl)-o-anisamide, hydrochloride (a) 5-Bromoacetyl salicylamide (515 g) was added to a stirred solution of dibenzylamine (750 g) in ethyl methyl ketone (3.0 l). The mixture was heated at reflux for one hour and the dibenzylamine hydrobromide was filtered and dried. The filtrate was allowed to cool, when the crude product crystallised. This was filtered off, dried, and recrystallised from ethyl acetate, (5 l), to give 5-(N,N-dibenzylglycyl)salicylamide as an off-white solid (336 g), m.p. 168°.

(b) 5-(N,N-Dibenzylglycyl)salicylamide (37.4 g) was heated at reflux for 2 hours with methyl iodide (10 ml) and anhydrous potassium carbonate (20 g) in ethyl methyl ketone (350 ml). The inorganic salts were filtered off and the solvent was evaporated in vacuo. The residue was dissolved in ethyl acetate, washed with water and again evaporated. The residual oil was crystallised from isopropanol to give 5-(N,N-dibenzylglycyl)-o-anisamide as a white solid, (14 g) m.p. 113°–114°.

(c) A solution of 5-(N,N-dibenzylglycyl)-o-anisamide (13.0g) in ethanol (800ml) was treated with excess solid sodium borohydride (ca.2g) and allowed to stand overnight at room temperature. The ethanol was then evaporated under reduced pressure and the residue partitioned between ethyl acetate and water. The ethyl acetate was separated, washed with brine, dried over MgSO$_4$ and evaporated. The residue readily crystallised on trituration with ether to afford 5-(2-dibenzylamino-1-hydroxyethyl)-o-anisamide as a white solid (11.1g) m.p. 120°–123°.

(d) The dibenzylamino alcohol as dissolved in ethanol (50 ml) and added to a pre-reduced suspension of palladium on carbon (10% 1g) in ethanol (20 ml). The mixture was hydrogenated until uptake was complete. Removal of the catalyst and solvent left 5-(2-amino-1-hydroxyethyl)-o-anisamide as a colourless gum which slowly solidified (2.1 g) m.p. 114.4°.

The base (2g) was dissolved in ethanol and treated with ethereal hydrogen chloride to afford the hydrochloride (1.3g) as a buff solid m.p. 219.7°.

This compound may be used in alkylation reactions to give the compounds in which $R^4$ is not a hydrogen atom.

EXAMPLE 6

5-[1-Hydroxy-2-[(1-methyl-3-phenylpropyl)amino]ethyl]-2-methoxymethoxy)benzamide (a) 5-(N,N-Dibenzylglycyl) salicylamide (37.4g) was dissolved with heating in methyl ethyl ketone (500 ml). The solution was cooled and stirred whilst a solution of sodium hydroxide (4.4g) in water (50 ml) was added. The mixture was stirred for a further hour and the solid filtered, washed with methyl ethyl ketone followed by ether, and dried at 40° C to give the sodium salt of 5(N,N-dibenzylglycyl) salicylamide (30.0g). The sodium salt (3.96g) was suspended in methyl ethyl ketone (100ml) and chlorodimethyl ether (1 ml) in benzene (5 ml) was added. The mixture was stirred for 2 hours then filtered. The filtrate was evaporated in vacuo to give yellow oil which was dissolved in isopropyl acetate and allowed to crystallise. The solid was filtered and dried to give 5-(N,N-dibenzylglycyl)-2-(methoxymethoxy) benzamide as a white crystalline solid (2.6 g) m.p. 127.5°.

(b) The methoxy methyl ether (4.18g) was suspended in methanol (250 ml) and benzyl acetone (1.7 g) was added with 10% PdO/C (0.5g) and 5% Pt/C (1.0g) in an ethanol (10 ml) slurry. The mixture was hydrogenated for 2 hours at 50°, filtered and evaporated to dryness in vacuo. The residual gum as dissolved in isopropyl acetate, filtered and allowed to crystallise to give 5-[1-hydroxy-2-[1-methyl-3-phenylpropyl)amino]ethyl]-2-(methoxymethoxy) benzamide as a white crystalline solid (2.1g) m.p. 102° C. This was recrystallised from isopropyl acetate to give m.p. 106° C.

EXAMPLE 7

5[2-[(1,1-Dimethyl-3-phenylpropyl)amino]-1-hydroxyethyl]-o-anisamide.

(a) 5-[N-Benzyl-N-(1,1-dimethyl-3-phenylpropyl)-glycyl]-o-anisic acid, methyl ester hydrochloride.

A solution of 5-bromoacetyl-o-anisic acid methyl ester (2.0g) and N-benzyl-1,1-dimethyl-3-phenylpropylamine (3.7g) in ethyl methyl ketone (30 ml) was refluxed for 20 hours, evaporated and the residue treated with ether. Precipitated amine hydrobromide (2.25g) was removed by filtration and the ethereal filtrate was treated with an excess of ethanolic hydrogen chloride. The solid that formed was removed to yield the hydrochloride (2.0g) m.p. 168°–169°.

(b) 5-[2-[(1,1-dimethyl-3-phenylpropyl)amino]-1-hydroxyethyl]-o-anisamide.

The above hydrochloride (1.7g) in ethanol (50 ml) was reduced by hydrogen at room temperature in presence of 10% palladium charcoal catalyst (0.5g). When reduction was complete (2 hr.) the catalyst was removed and washed with hot methanol. Solvents were removed from the solution and washings by evaporation, and the residue was treated in methanol (100 ml) with ammonia solution (d. 1.880; 100 ml.). After 44 hr. the solution was evaporated under reduced pressure to give the amide hydrochloride, m.p. 163°–165° when recrystallised from ethanol.

EXAMPLE 8

2-Allyloxy-5-[1-hydroxy-2-[(1-methyl-3-phenylpropyl)amino]ethyl] benzamide, hydrochloride 5-[1-Hydroxy-2-[1-methyl-3-phenylpropyl)amino]ethyl] salicylamide (8.0g), suspended in ethanol (80.ml) and a solution of sodium (0.6g) in ethanol (30 ml) was treated with allyl bromide (2 ml.). After 4 hr. at the reflux the mixture was evaporated, the residue dissolved in ether and water and the ethereal layer was extracted with 2N sodium hydroxide solution (3 × 50 ml.) and water 2 × 50 ml.). The dried ethereal solution was evaporated to yield an oil that was treated with a slight excess of ethanolic hydrogen chloride and ethyl acetate. The crystalline hydrochloride that formed was recrystallised from isopropanol to give the amide hydrochloride (0.9g) m.p. 158°–160°.

EXAMPLE 9

Pharmaceutical compositions

Capsules

To prepare 10,000 capsules each containing 20 mg active ingredient

Mix together 200 g. powdered active ingredient with a sufficient quantity of microcrystallin cellulose B.P.C. and fill into No. 3 hard gelatin capsules so that each capsule contains about 120 mg. of the mixture.

Capsules may similarly be prepared each containing 50 mg. active ingredient

Tablets

To prepare 5,000 tablets each containing 100 mg. active ingredient

Mix together 500 g. active ingredient, 490 g. microcrystalline cellulose B.P.C., 5 g. magnesium stearate and 5 g. stearic acid B.P. Compress the powders on a suitable tableting press to produce tablets each ¼ inch in diameter and weighing about 200 mg.

To prepare 5,000 tablets each containing 200 mg. active ingredient

Mix together 1,000 active ingredient, 500 g lactose and 175 g. maize starch and sufficient of a 2% aqueous solution of sodium hydroxyethyl cellulose to produce a damp cohesive mass. Pass the damp mass through a No. 14 mesh B.S.S. sieve and dry in a fluidised bed dryer at 60° C. Pass the dried granules through a No. 22 B.S.S. sieve and mix with 60 g. dried maize starch and 15 g. magnesium stearate. Compress the lubricated granules on suitable tableting press using ⅜ inch deep concave punches to produce tablets each weighing about 350 mg.

These tablets may be film coated with suitable film forming material such as methyl cellulose, hydroxypropylmethyl cellulose or ethyl cellulose or mixtures of these materials using standard techniques.

The tablets may also be sugar coated by the standard sugar coating techniques.

Injection

To prepare an injection containing 10 m.g. active ingredient per ml.

Dissolve 10 g active ingredient and 7.5 g. sodium chloride in 950 ml. water for injection. When solution is complete made up to 1 liter with more water for injection. Subdivide the solution into suitable size ampoules (1 ml., 5 ml., or 10 ml.) seal and sterilize by heating in an autoclave.

The "active ingredient" used in these compositions is 5-[1-hydroxy-2-(1-methyl-3-phenylpropyl)aminoethyl]-o-anisamide, the preparation of which is described in Example 3.

What is claimed is:

1. A compound of the formula:

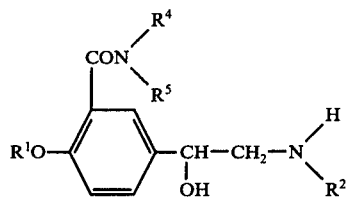

in which $R^1$ is a lower alkenyl or alkoxy lower alkyl radical; $R^2$ is 1-methyl-3-phenylpropyl or 1,1-dimethyl-3-phenylpropyl and $R^4$ and $R^5$ are each a hydrogen atom or a lower alkyl radical; or a physiologically acceptable acid addition salt thereof.

2. The compound of claim 1 wherein $R^1$ is alkenyl of up to 4 carbon atoms and lower alkyl is from 1 to 4 carbon atoms.

3. The compound of claim 2 which is 2-allyloxy-5-[1-hydroxy-2-[(1-methyl-3-phenylpropyl)amino]ethyl]-benzamide or a physiologically acceptable acid addition salt thereof.

4. The compounds of claim 3 which is 2-allyloxy-5-[1-hydroxy-2-[(1-methyl-3-phenylpropyl)amino]ethyl]-benzamide hydrochloride.

* * * * *